US008983951B2

(12) United States Patent
Friedlander et al.

(10) Patent No.: US 8,983,951 B2
(45) Date of Patent: *Mar. 17, 2015

(54) TECHNIQUES FOR RELATING DATA IN HEALTHCARE DATABASES

(75) Inventors: Robert R. Friedlander, Southbury, CT (US); Anwer M. Khan, Irvine, CA (US)

(73) Assignee: International Business Machines Corporation, Armonk, NY (US)

(*) Notice: Subject to any disclaimer, the term of this patent is extended or adjusted under 35 U.S.C. 154(b) by 1972 days.

This patent is subject to a terminal disclaimer.

(21) Appl. No.: 11/850,866

(22) Filed: Sep. 6, 2007

(65) Prior Publication Data

US 2007/0299691 A1    Dec. 27, 2007

Related U.S. Application Data

(63) Continuation of application No. 11/029,840, filed on Jan. 4, 2005, now Pat. No. 7,580,922.

(51) Int. Cl.
*G06F 17/30* (2006.01)
*G06F 19/00* (2011.01)
*G06Q 50/22* (2012.01)

(52) U.S. Cl.
CPC ............ *G06F 19/322* (2013.01); *G06F 19/363* (2013.01); *G06Q 50/22* (2013.01); *Y10S 707/957* (2013.01)
USPC ........... 707/736; 707/738; 707/741; 707/802; 707/803; 707/957; 707/E17.002; 707/E17.056; 707/E17.057; 705/2; 705/3

(58) Field of Classification Search
CPC .................. G06F 17/30321; G06F 17/30333; G06F 17/30592; Y10S 707/941
USPC ................ 707/736, 738, 741, 802, 803, 957, 707/E17.002, E17.056, E17.057, 999.102; 705/2, 3
See application file for complete search history.

(56) References Cited

U.S. PATENT DOCUMENTS

| 4,328,978 A | 5/1982 | McLaughlin | |
| 5,594,899 A * | 1/1997 | Knudsen et al. | 1/1 |

(Continued)

FOREIGN PATENT DOCUMENTS

| JP | 2002312373 | 4/2001 |
| JP | 2002342484 | 2/2002 |
| WO | WO 01/08077 A1 | 2/2001 |

OTHER PUBLICATIONS

Song et al., "An Analysis of Many-to-Many Relationships Between Fact and Dimension Tables in Dimensional Modeling", In Proceedings of the International Workshop on Design and Management of Data Warehouses (DMDW' 2001), Jun. 4, 2001, pp. 13.*

(Continued)

*Primary Examiner* — Phuong Thao Cao
(74) *Attorney, Agent, or Firm* — Yudell Isidore PLLC; John Pivnichny

(57) ABSTRACT

Systems and computer program products for relating facts stored in healthcare databases are provided. At least two fact tables stored in a healthcare database including data meeting a criteria of interest are located. An identification key is assigned to the at least two fact tables including the located data meeting the criteria of interest. The identification key provides access to a dimension table including a list of subjects associated with the at least two fact tables including the located data meeting the criteria of interest so as to allow future identification of the subjects meeting the criteria of interest.

13 Claims, 5 Drawing Sheets

(56) References Cited

U.S. PATENT DOCUMENTS

| | | | |
|---|---|---|---|
| 5,778,354 A * | 7/1998 | Leslie et al. | 707/715 |
| 5,828,809 A * | 10/1998 | Chang et al. | 386/241 |
| 5,903,890 A * | 5/1999 | Shoji et al. | 1/1 |
| 5,926,818 A * | 7/1999 | Malloy | 1/1 |
| 5,960,194 A * | 9/1999 | Choy et al. | 1/1 |
| 6,016,497 A * | 1/2000 | Suver | 1/1 |
| 6,058,391 A | 5/2000 | Gardner | |
| 6,189,004 B1 * | 2/2001 | Rassen et al. | 1/1 |
| 6,192,357 B1 * | 2/2001 | Krychniak | 1/1 |
| 6,212,524 B1 * | 4/2001 | Weissman et al. | 707/600 |
| 6,377,993 B1 | 4/2002 | Brandt et al. | |
| 6,385,604 B1 | 5/2002 | Bakalash et al. | |
| 6,509,898 B2 | 1/2003 | Chi et al. | |
| 6,578,043 B2 | 6/2003 | Nye | |
| 6,629,106 B1 | 9/2003 | Narayanaswamy et al. | |
| 6,691,122 B1 * | 2/2004 | Witte et al. | 706/47 |
| 6,714,979 B1 | 3/2004 | Brandt et al. | |
| 6,735,605 B2 * | 5/2004 | Bird et al. | 1/1 |
| 6,782,350 B1 * | 8/2004 | Burnley et al. | 702/186 |
| 6,963,826 B2 * | 11/2005 | Hanaman et al. | 703/2 |
| 7,188,170 B1 * | 3/2007 | Burnley et al. | 709/224 |
| 7,191,183 B1 * | 3/2007 | Goldstein | 707/602 |
| 7,349,868 B2 * | 3/2008 | Tenorio | 705/26.62 |
| 7,383,280 B2 * | 6/2008 | Kornelson et al. | 1/1 |
| 7,558,808 B2 * | 7/2009 | Mason et al. | 1/1 |
| 7,580,922 B2 * | 8/2009 | Friedlander et al. | 1/1 |
| 7,739,224 B1 * | 6/2010 | Weissman et al. | 707/794 |
| 8,122,044 B2 * | 2/2012 | Yeh et al. | 707/760 |
| 2002/0059183 A1 | 5/2002 | Chen | |
| 2002/0099691 A1 | 7/2002 | Lore et al. | |
| 2002/0099692 A1 | 7/2002 | Shah et al. | |
| 2002/0156791 A1 | 10/2002 | Nesamoney et al. | |
| 2002/0184225 A1 | 12/2002 | Ghukasyan | |
| 2003/0055832 A1 * | 3/2003 | Roccaforte | 707/100 |
| 2003/0074222 A1 | 4/2003 | Rosow et al. | |
| 2003/0088438 A1 * | 5/2003 | Maughan et al. | 705/2 |
| 2003/0126148 A1 | 7/2003 | Gropper et al. | |
| 2003/0144988 A1 * | 7/2003 | Nareddy et al. | 707/1 |
| 2003/0177132 A1 * | 9/2003 | Thomas et al. | 707/100 |
| 2003/0191669 A1 | 10/2003 | Fitzgerald et al. | |
| 2003/0195898 A1 | 10/2003 | Agarwal et al. | |
| 2004/0054683 A1 * | 3/2004 | Nishizawa et al. | 707/102 |
| 2004/0199517 A1 * | 10/2004 | Casati et al. | 707/100 |
| 2005/0075949 A1 * | 4/2005 | Uhrig et al. | 705/28 |
| 2005/0076036 A1 * | 4/2005 | Le | 707/100 |
| 2005/0246189 A1 | 11/2005 | Monitzer et al. | |
| 2006/0149705 A1 * | 7/2006 | Friedlander et al. | 707/2 |
| 2006/0206462 A1 * | 9/2006 | Barber | 707/3 |
| 2006/0218157 A1 * | 9/2006 | Sourov et al. | 707/100 |
| 2007/0061450 A1 * | 3/2007 | Burnley et al. | 709/224 |

OTHER PUBLICATIONS

Hotelling, H., Office Action dated Apr. 30, 2007, U.S. Appl. No. 11/029,840.

Hotelling, H., Office Action dated Nov. 7, 2007, U.S. Appl. No. 11/029,840.

Hotelling, H., Office Action dated May 27, 2008, U.S. Appl. No. 11/029,840.

Hotelling, H., Office Action dated Nov. 7, 2008, U.S. Appl. No. 11/029,840.

Hotelling, H., Notice of Allowability dated Apr. 16, 2009, U.S. Appl. No. 11/029,840.

"Lab4" web page archived on Jul. 11, 2004 at: http://web.archive.org/web/20040711205854/http://www-users.cs.umn.edu/~mckoskey/CSCI5708_databases/original/lab4.html.

* cited by examiner

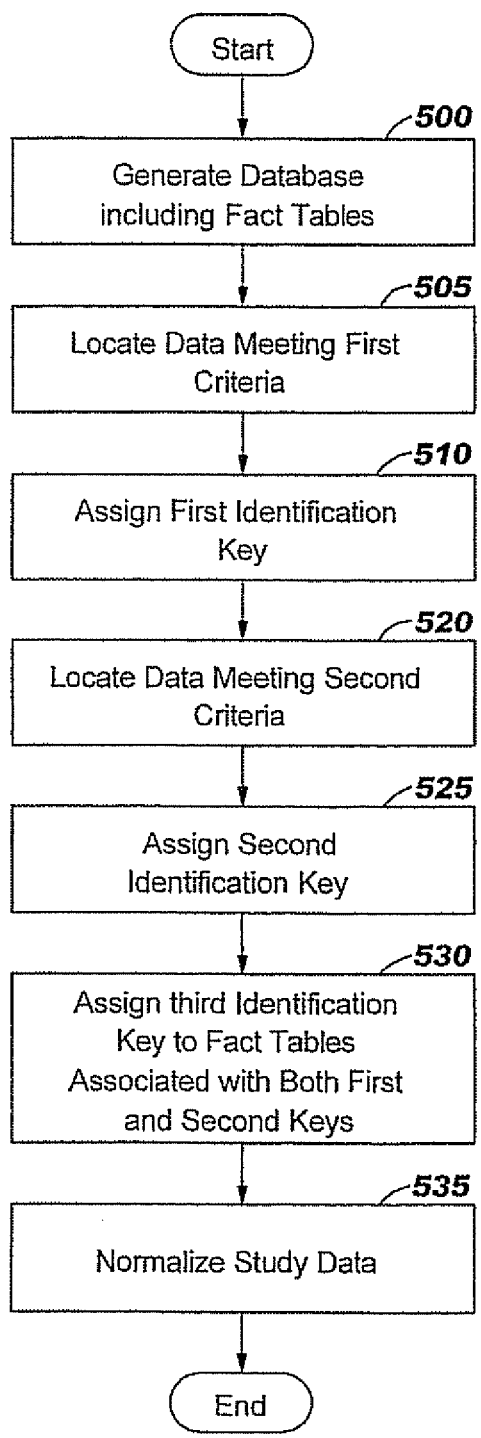

TECHNIQUES FOR RELATING DATA IN HEALTHCARE DATABASES

RELATED APPLICATION

The present application claims the benefit of priority as a continuation of U.S. application Ser. No. 11/029,840, filed Jan. 4, 2005, issued as U.S. Pat. No. 7,580,922, which is entitled "METHODS FOR RELATING DATA IN HEALTHCARE DATABASES," the disclosure of which is hereby incorporated herein by reference as if set forth in its entirety.

FIELD OF THE INVENTION

The invention relates to database management in general and, more particularly, to organization of and access to data stored in databases.

BACKGROUND OF THE INVENTION

As the field of healthcare continues to become more specialized, the provision of services by many healthcare workers and/or providers to many patients may increase. In order to accomplish this, healthcare delivery has been organized into specialized departments or healthcare sources such as, for example, nursing, laboratory, pharmacy, and radiology departments. Each department has the responsibility for accomplishing its particular, often specialized, subset of tasks. Sometimes the departments are associated with different healthcare enterprises or offices having different geographic locations. Unfortunately, this has resulted in suboptimal healthcare operations because patient information related to a single patient that is stored at various departments may not be easily accessible from a single place.

This patient information, or medical data, may be stored in a database environment configured to store large volumes of data. Furthermore, the medical data stored in the database environment may be processed by, for example, searching the stored medical data. Details with respect to conventional methods for storing and/or accessing medical data in and/or from databases is discussed in, for example, United States Patent Publication Nos. US 2003/0088438 and US 2003/0177132.

However, as the amount of available medical data expands, it may become increasingly difficult to store and/or access the medical data, especially for research and comparison purposes. For example, use of the medical data for purposes of diagnosing various medical conditions and/or researching medical areas may be very difficult. Accordingly, there is a need to improve storage of and access to medical data.

SUMMARY OF THE INVENTION

Some embodiments of the present invention provide systems and computer program products for relating facts stored in healthcare databases. At least two fact tables stored in a healthcare database including data meeting a criteria of interest are located. An identification key is assigned to the at least two fact tables including the located data meeting the criteria of interest. The identification key provides access to a dimension table including a list of subjects associated with the at least two fact tables including the located data meeting the criteria of interest so as to allow future identification of the subjects meeting the criteria of interest.

In further embodiments of the present invention, at least two fact tables stored in the healthcare database including data meeting a second criteria of interest may be located. A second identification key may be assigned to the at least two fact tables including the located data meeting the second criteria of interest. The second identification key may provide access to a second dimension table including a list of subjects associated with the at least two fact tables including the second criteria of interest so as to allow future identification of the subjects meeting the second criteria of interest. A third identification key may be assigned to subjects meeting the first and second criterion of interest. The third identification key may provide access to a third dimension table including a list of subjects meeting both the first and second criterion of interest so as to allow future identification of the subjects meeting the first and second criterion of interest. In certain embodiments of the present invention, the third identification key may be automatically assigned.

In still further embodiments of the present invention, the located data may be associated with a medical study. The data associated with the medical study may be normalized so as to allow direct comparison of the data.

In some embodiments of the present invention, a database may be generated including a plurality of fact tables and a plurality of associated dimension tables. The plurality of fact tables may be divided into a plurality of groups of fact tables and each of the plurality of groups may be associated with an entity. Authorization codes may be provided to each entity, which provide access to at least one of the groups of fact tables. The plurality of fact tables may include at least one identification key which identifies an associated dimension table. The associated dimension table may include information that further describes facts provided in the fact table. The plurality of fact tables may be related through the plurality of dimension tables.

BRIEF DESCRIPTION OF THE DRAWINGS

FIG. 5 is flowchart illustrating operations according to further embodiments of the present invention.

DETAILED DESCRIPTION OF EMBODIMENTS OF THE INVENTION

Figure 1:
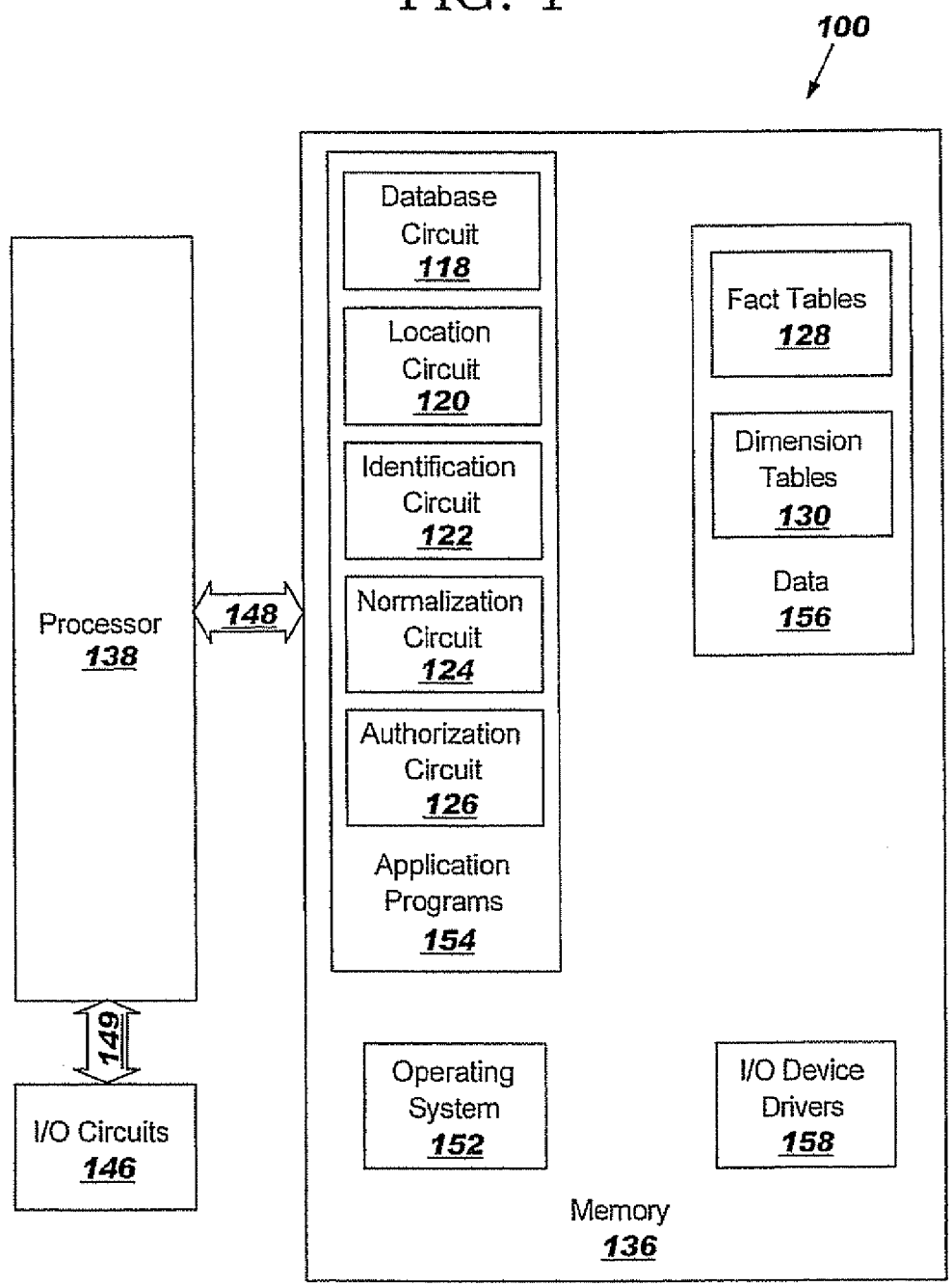
FIG. 1 is a block diagram illustrating data processing systems according to some embodiments of the present invention.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

It will be understood that, although the terms first, second, etc. may be used herein to describe various elements, these elements should not be limited by these terms. These terms are only used to distinguish one element from another element. Thus, a first element discussed below could be termed a second element without departing from the scope of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will be appreciated by one of skill in the art, the invention may be embodied as a method, data processing system, or computer program product. Accordingly, the present invention may take the form of an entirely hardware embodiment, an entirely software embodiment or an embodiment combining software and hardware aspects all generally referred to herein as a "circuit" or "module." Furthermore, the present invention may take the form of a computer program product on a computer-usable storage medium having computer-usable program code embodied in the medium Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language or in a visually oriented programming environment, such as VisualBasic.

The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The invention is described in part below with reference to flowchart illustrations and/or block diagrams of methods, systems, computer program products and data structures according to embodiments of the invention. It will be understood that each block of the illustrations, and combinations of blocks, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Embodiments of the present invention will now be discussed with respect to FIGS. 1 through 5. FIG. 1 illustrates an exemplary data processing system 100 or database environment that may be included in devices operating in accordance with some embodiments of the present invention. As illustrated, the data processing system 100 includes a processor 138, a memory 136 and input/output circuits 146. The data processing system 100 may be incorporated in, for example, a personal computer, server, router or the like. The processor 138 communicates with the memory 136 via an address/data bus 148 and communicates with the input/output circuits 146 via an address/data bus 149. The input/output circuits 146 can be used to transfer information between the memory 136 and another computer system or a network using, for example, an Internet Protocol (IP) connection. These components may be conventional components such as those used in many conventional data processing systems, which may be configured to operate as described herein.

In particular, the processor 138 can be any commercially available or custom microprocessor, microcontroller, digital signal processor or the like. The memory 136 may include any memory devices containing the software and data used to implement the functionality circuits or modules used in accordance with embodiments of the present invention. The memory 136 can include, but is not limited to, the following types of devices: cache, ROM, PROM, EPROM, EEPROM, flash memory, SRAM, DRAM and magnetic disk. In some embodiments of the present invention, the memory 136 may be a content addressable memory (CAM).

As further illustrated in FIG. 1, the memory 136 may include several categories of software and data used in the data processing system 100: an operating system 152; application programs 154; input/output device drivers 158; and data 156. As will be appreciated by those of skill in the art, the operating system 152 may be any operating system suitable for use with a data processing system, such as OS/2, AIX or zOS from International Business Machines Corporation, Armonk, N.Y., Windows95, Windows98, Windows2000 or WindowsXP from Microsoft Corporation, Redmond, Wash., Unix or Linux. The input/output device drivers 158 typically include software routines accessed through the operating system 152 by the application programs 154 to communicate with devices such as the input/output circuits 146 and certain memory 136 components. The application programs 154 are illustrative of the programs that implement the various features of the circuits and modules according to some embodiments of the present invention. Finally, the data 156 represents the static and dynamic data used by the application programs 154, the operating system 152, the input/output device drivers 158, and other software programs that may reside in the memory 136. As illustrated in FIG. 1, the data 156 may include fact tables 128 and dimension tables 110 for use by the circuits and modules of the application programs 154 according to some embodiments of the present invention as discussed further herein.

As used herein, "fact tables" 128 refer to tables that include or store a value corresponding to an observed value. For example, the fact table may include a test result, a patient's blood pressure, a date of a lab test, and the like. The fact tables also include one or more identification keys. The identification keys may be a symbol, a series of numbers or letters or any combination thereof. The identification keys identify dimension tables 130 associated with the facts table in which they are identified. The dimension tables provide additional information about the observation stored in the fact table 128. For example, a "dimension table" 130 accessed using the associated identification key stored in the fact table may include information about the test performed that provided the result stored in the fact table, information about the patient, information about the provider, information about the person who requested the test or authorized the test, the date and/or time of the test, international standards and the like. The dimension tables 130 may allow drilling in and out of the data stored in the dimension tables 130. For example, if the dimension table 130 associated with the date is accessed using the associated identification key, the date of the test may be drilled out to the week of the test, the month of the test, the year of the test etc. as will be discussed further herein.

Medical data according to embodiments of the present invention may be stored in databases using the Ralph Kimball approach. The Ralph Kimball approach is known to those having skill in the art and, therefore, will not be discussed in detail herein. The Ralph Kimball approach is discussed at rkimball.com. As discussed above, facts or atomic data are stored in fact tables 128 including one or more identification keys which are associated with corresponding dimension tables 130. A single fact table 128 and the associated dimension table(s) 130 form a star schema, the fact table 128 being the center of the star and the dimension tables 130 being the arms. Two or more star schemas form a constellation schema. The facts stored in the fact tables 128 may be associated with each other through the dimension tables 130. For example, if a patient has three tests performed, each test and test result may be stored in a corresponding fact table 128. However, each of these fact tables 128 may have an identification key for the patient, which accesses the patients dimension table 130. Thus, the tests and test results may all be associated through the patient dimension table as discussed further herein.

Referring again to FIG. 1, according to some embodiments of the present invention the application programs 154 include a database circuit 118, a location circuit 120, an identification circuit 122, a normalization circuit 124 and an authorization circuit 126. The database circuit 118 may be configured to generate a database including a one or more fact tables 128 and one or more associated dimension tables 130 as discussed above. The location circuit 120 may be configured to receive a criteria of interest, such as a type of medical condition, for example, diabetes. As used herein, a "criteria of interest" may include any information or statistic that may provide useful information for medical research purposes. For example, a criteria of interest may be a test result, a medical condition, the presence or absence of a gene, the presence or absence of a protein, a medical procedure and the like. The location circuit 120 is further configured to locate the criteria of interest in one or more fact tables 128 stored in the database being searched. Once located, the identification circuit 122 may be configured to assign the subjects or patients associated with each of the located fact tables 128 an identification key. This may be referred to as "premarking" the subjects associated with the fact tables 128 including the criteria of interest. Premarking these subjects may enable future access to the subjects satisfying the criteria of interest without having to search the entire database again for the criteria of interest. The assigned identification key may be used to access a dimension table 130 that lists the subjects who satisfy the criteria of interest.

It will be understood that in some embodiments of the present invention, the patients having a criteria of interest, for example, a patient afflicted with diabetes, may be premarked as the information is entered into the database. For example, once the database circuit 118 has generated a database according to embodiments of the present invention, the "new" entries to the database may be premarked upon entry.

In some embodiments of the present invention, the location circuit 120 may be further configured to locate a second criteria of interest, for example, coronary artery disease (CAD), in one or more fact tables 128. Once located, the identification circuit 122 may be configured to assign the subjects associated with the fact tables including the second criteria of interest a second identification key, i.e., premark a second number of subjects. In certain embodiments of the present invention, the subjects associated with the first identification key and the subjects associated with the second identification key may be compared and the identification circuit may be configured to assign the subjects satisfying both criterion of interest, i.e., diabetes and CAD, a third identification key. The third identification key may allow access to an associated third dimension table, or compound index, which may list the subjects satisfying both criterion of interest.

In some embodiments of the present invention, the criteria of interest may be a patient's participation in a medical study, for example, the use of an experimental drug for curing cancer. As discussed above, the location circuit 120 may be configured to locate the patient's participating in the study and the identification circuit 122 may be configured to assign an identification key to the located patients so as to allow future access to this list of patients. If, for example, the results of the drug treatments for each of the patients participating in the study were to be compared, the outcome of the comparison may not provide useful information as each of the patients may be at different stages in the study. Some patients may have just received their first dose of the experimental drug, while others may have had twenty or more doses. Accordingly, the normalization circuit 124 may be configured to normalize the first doses of each of the patients such that the results of the comparison compare a first dose result of a first patient to a first dose result of a second patient, regardless of how many doses the patients have actually received at the present time.

The cost of developing the type of database discussed herein may be large, thus, in some embodiments of the present invention groups of entities, such as pharmaceutical companies, having a single goal, such as, researching a new drug for curing cancer, may pool their resources and generate a single database for use by all of the groups of entities. The group of entities may be termed a "club" and embodiments of the present invention including the club may be termed the "club model." In embodiments of the present invention using this "club model", the entities may not want to share results of their research, just the database resource. Thus, the authorization circuit 126 may be configured to provide an additional identification key assigned by the identification circuit 122 in the fact tables 128 of this database. The additional identification key may provide information as to which groups, entities, individuals etc. are allowed access to the facts in the fact table. Thus, access to the facts in the fact table may only be provided to those groups, entities, individuals etc. that are authorized to view them. Which groups, entities and individuals have access to what information can be changed at any time.

It will be understood that generation of databases according to embodiments of the present invention including application programs 154 may be performed in multiple fashions. For example, medical data may be physically instantiated, i.e., all medical data may be brought into a single database, federated, i.e., the medical data may be stored in remote database and links may be provided to those databases to provide access thereto, or a combination of the two without departing from the scope of the present invention.

While the present invention is illustrated with reference to the database circuit 118, the location circuit 120, the identification circuit 122, the normalization circuit 124 and the authorization circuit 126 being application programs in FIG. 1, as will be appreciated by those of skill in the art, other configurations fall within the scope of the present invention. For example, rather than being application programs 154, these circuits may also be incorporated into the operating system 152 or other such logical division of the data processing system 100. Furthermore, while the database circuit 118, the location circuit 120, the identification circuit 122, the normalization circuit 124 and the authorization circuit 126 are illustrated in a single data processing system, as will be appreciated by those of skill in the art, such functionality may be distributed across one or more data processing systems. Thus, the present invention should not be construed as limited to the configuration illustrated in FIG. 1, but may be provided by other arrangements and/or divisions of functions between data processing systems. For example, although FIG. 1 is illustrated as having various circuits, one or more of these circuits may be combined without departing from the scope of the present invention.

Figure 2:
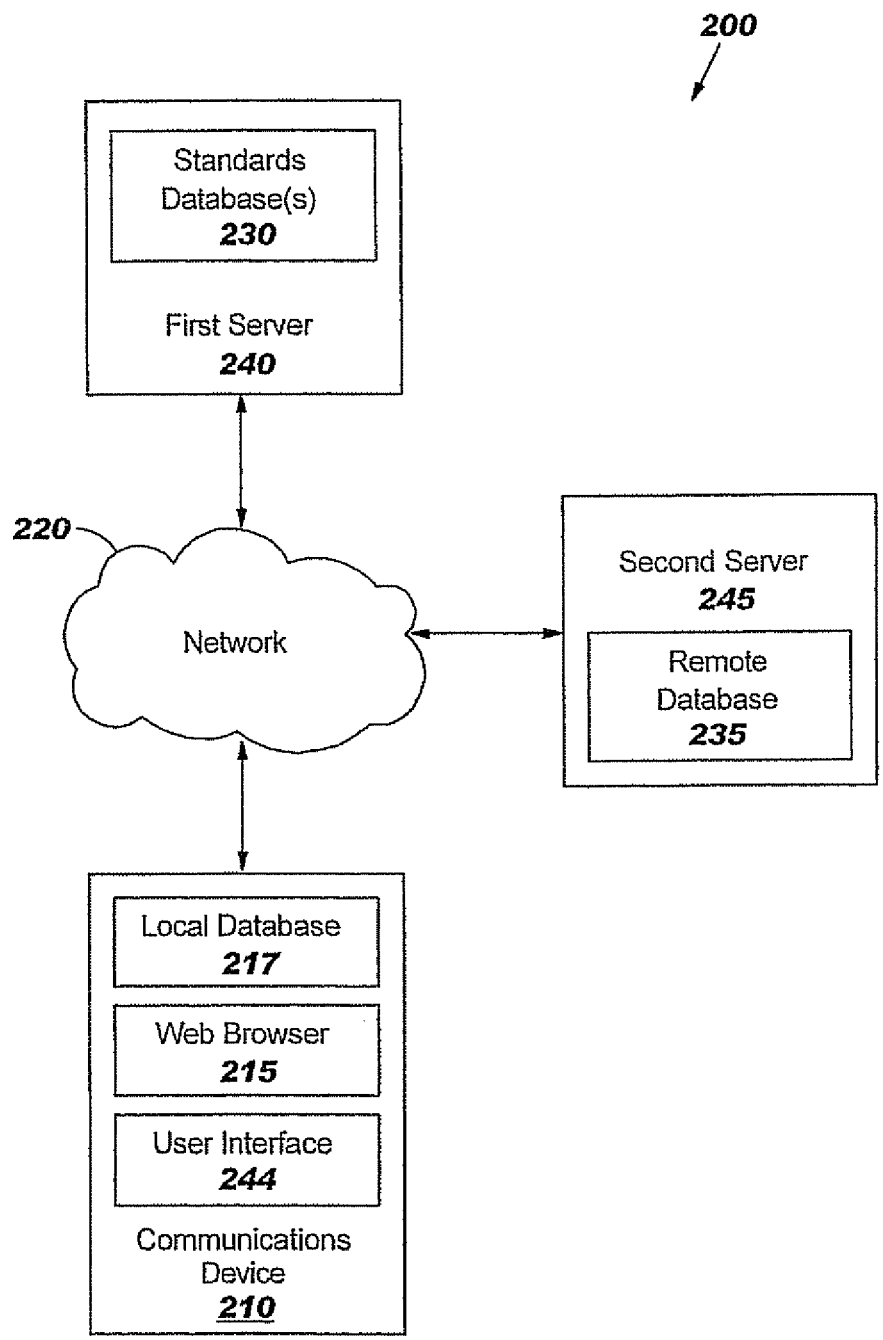
FIG. 2 is a block diagram illustrating an exemplary network environment for operations and devices according to some embodiments of the present invention.

FIG. 2 illustrates an exemplary environment 200 for operations and devices according to some embodiments of the present invention. As illustrated in FIG. 2, the environment 200 may include a communications device 210, a network 220, a first server 240 and a second server 245. It will be understood that the communications device 210 illustrated in FIG. 2 may include the data processing system 100 discussed above with respect to FIG. 1. For example, the application programs 154 discussed with respect to FIG. 1 could be included as part of the local database 217 of the communications device 210. The communications device 210 may be, for example, a laptop computer, a desktop computer, a personal data assistant (PDA), a web capable mobile terminal or any device capable of communicating with the network 220. The communications device 210 may include a user interface 244, which may be used to enter queries for criterion of interest, a web browser 215 that may be accessed through the user interface 244, and a local database 217 according to embodiments of the present invention. The local database 217 may include, for example, medical data which has been instantiated from other sources. The first server 240 may include a standards database 230 including international standards as discussed further below. The second server 245 may include a remote database 235, which may include medical data which may be accessed by the local database 217 according to embodiments of the present invention. In other words, the remote database 235 may be federated. The communications device 210 may communicate over the network 220, for example, the internet, through a telephone line, a digital subscriber link (DSL), a broadband cable link, a wireless link or the like. The first and second servers 240 and 245 may also communicate over the network 220. Thus, the network 220 may convey data between the communications device 210 and the first and second servers 240 and 245.

Exemplary operations of methods and devices according to some embodiments of the present invention will now be discussed with respect to FIG. 2. A researcher may be researching a cause of diabetes. The researcher may have access to a communications device 210 including a database 217 according to some embodiments of the present invention. The research may enter "blood test positive for diabetes" as the criteria of interest using the user interface 244 of the communications device 210. For example, the user interface 244 may be a graphical interface that receives a query, for example, the criteria of interest. Devices and methods according to embodiments of the present invention may be configured to located one or more fact tables in the local database 217 or the federated database 235 including the criteria of interest. It will be understood that although the local database 217 is illustrated as being stored at the communications device 210, the local database 217 may be stored at a remote server associated with the communications device 210 without departing from the scope of the present invention.

Once the fact tables including diabetes are located, the database may premark these fact tables by assigning each of the fact tables the same identification key, which may be stored in the fact table with other identification keys. The identification key may be used to access a dimension table, which may list all the patient identification keys for patients associated with the fact tables including data that matches the criteria of interest. Thus, the fact tables associated with diabetes and the patients associated therewith may be easily accessible in the future without searching the entire database 217 again.

Figure 3:
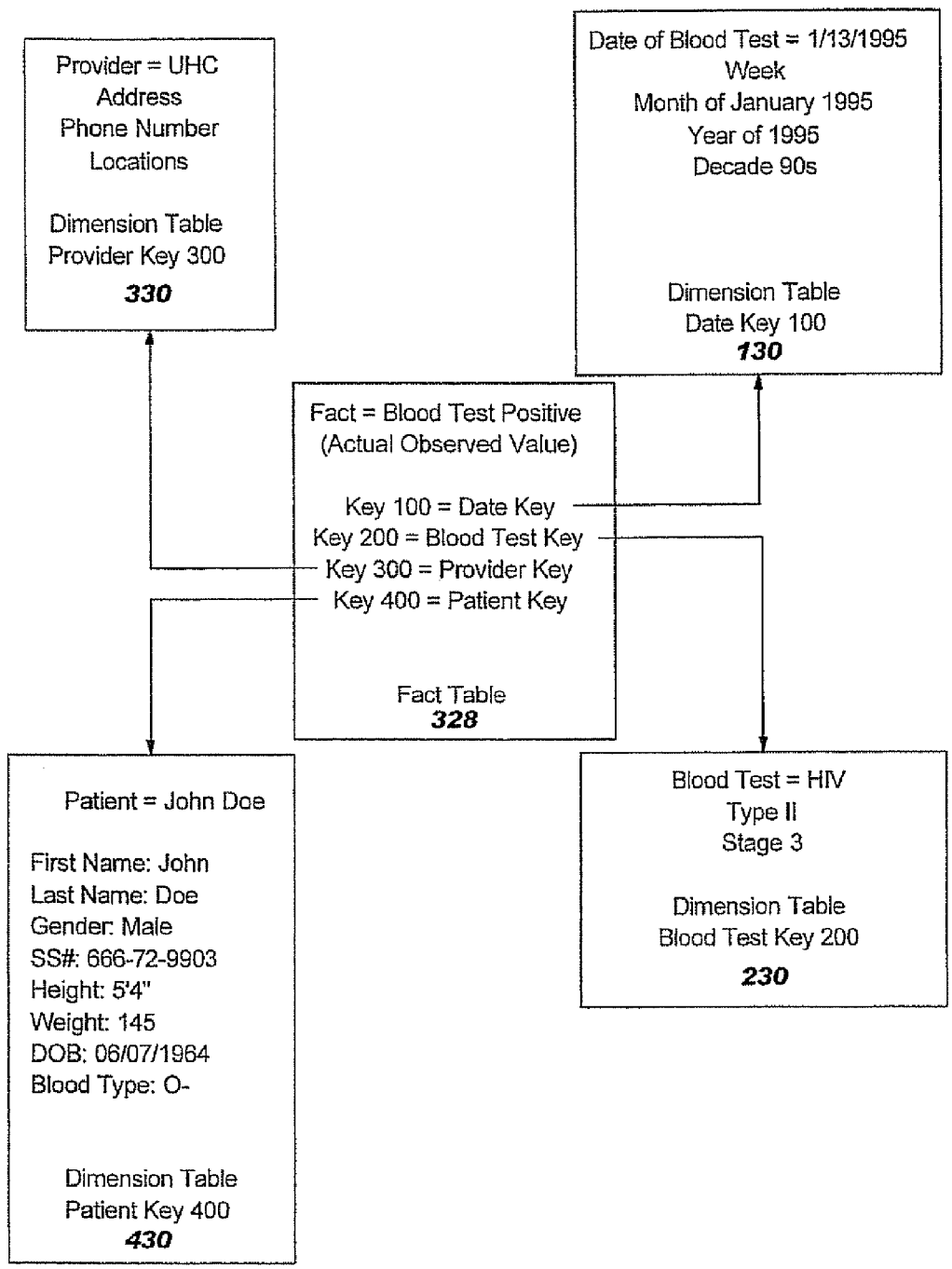
FIG. 3 is a schematic illustration of fact tables and dimension tables creating a star schema according to some embodiments of the present invention.

A schematic illustration of an exemplary fact table and associated dimension tables is illustrated in FIG. 3. As illustrated therein, the fact table 328 is provided for an observation that this patient's blood tested positive for diabetes. The fact table 328 also includes identification keys 100 through 400, which identify different dimension tables associated with the fact table 328. It will be understood that FIG. 3 is only an exemplary embodiment of fact tables and dimension tables according to some embodiments of the present invention and, therefore, embodiments of the present invention should not be limited to the configuration illustrated therein. For example, more or less than four dimension tables may be provided without departing from the teachings of the present invention.

As further illustrated in FIG. 3, the date key 100 provides access to the date dimension table 130. The date dimension table may provide information about the date of the blood test was taken. As further illustrated, the information provided in the date dimension table may also be drilled out to the week, month or year in which the test was taken. Similarly, the blood test key 200 provides access to the blood test dimension table 230. The blood test dimension table may provide information about the blood test, for example, the positive blood test was for type II diabetes in stage 3. This information may be drilled out beyond the blood test level to all blood tests for this patient, all blood tests for any patients having similar results and the like.

Referring again to FIG. 3, the provider key 300 provides access to the provider dimension table 330. The provider dimension table may provide information about the patient's healthcare provider, for example, United Healthcare (UHC). This dimension table 330 may include the provider's address, telephone number, copay, locations and the like. Finally, the patient key 400 provides access to the patient dimension table 430, which provides information about the patient having the positive blood test. As illustrated in FIG. 3, the patient dimension table may include the patient's first and last name, gender, social security number, height, weight, date of birth, blood type and the like.

The dimension tables according to some embodiments of the present invention may be expanded to provide a broader view of the information available in the database or a narrower view of the information provided in the database (drill in and out). For example, the criteria of interest may be a adverse reaction to a particular drug. The results of this query may be quite large as the "adverse reaction" may range from a rash to death. Thus, the information may be narrowed to just those patients who experienced a rash as a result of taking the drug. The information may be further narrowed to look at each patient experiencing the rash individually or patients that are women between the ages of 20 and 40. Furthermore, the type of drug may be expanded to provide all of the drugs in the particular class of drugs. These examples of drilling in and out of the data are provided for exemplary purposes only and, therefore, embodiments of the present invention are not be limited to these examples.

Referring again to FIG. 2, the researcher may enter a second criteria of interest, for example, heart disease, using the user interface 244 of the communications device 210. The second criteria of interest may be located in one or more fact tables in the local database 217 or the federated database 235. Once the fact tables including heart disease are located, the database may premark the fact tables by assigning each of the fact tables the same identification key. The second identification key may be used to access a second dimension table, which may list all the patient identification keys associated with the fact tables that match the second criteria of interest. Furthermore, the fact tables and associated patient records identified by the first and second identification keys may be searched to determine if any of these patients associated with the fact tables identified satisfy both the first and second criterion of interest (diabetes and heart disease). If any of the patient associated with the fact tables identified satisfy both criterion of interest, these patients may be provided a third identification key which accesses a third dimension table listing all the patients identification keys associated with the fact tables meeting both criterion. Thus, the results of the first and second searches may be combined to provide a compound index in the third dimension table to provide even more detailed information. Premarking the first, second and third groups of patients may allow future access to this information without having to search through the entire database 217 again.

In some embodiments of the present invention, the database 217 may be configured to automatically premark compound indexes based on previous queries done by the researcher. In other words, some embodiments of the present invention may be extended to include automated learning to discover new types of combinations of criteria that of interest based on, for example, actual queries or text mining of medical data and/or literature.

The web browser 215 may be used to access other databases, for example, standards databases 230, such as Logical Observation Identifiers Names and Codes (LOINC) and SNOMED clinical terms (SNOMED CT). These standards databases 230 may be used to translate, for example, test results, into a national format so that any researcher in any part of the world may be able to access and understand the test results. For example, the test may be a cholesterol panel. A national standard for a cholesterol panel may have five different results including HDL, LDL and so on. In a local hospital the cholesterol panel may have seven results. Thus, using LOINC the results of the local cholesterol panel having seven results may also be stored in the database 217 using the national format of five different results. Thus, when non-local researchers access the results, they will understand the information provided in the database.

In some embodiments of the present invention, the local database 217 may be shared among several groups of people who are all interested in the solving the same problem. For example, five pharmaceutical companies (a club) may all be interested in developing a drug to cure cancer. Each of the pharmaceutical companies may perform research on the drug and store the results of their research in the database 217. When a new fact or research result is entered into the database 217, an identification key may be included in the fact table that identifies a dimension table including a list of people who are authorized to view these facts. Thus, the pharmaceutical companies can share certain information with each other and retain certain information internally and still share the cost of the database 217.

In some embodiments of the present invention, the database 217 may be used by an entity performing a controlled study, for example, a controlled study for an experimental drug. Individuals may enter the study at various times and, therefore, may all be at different stages of their treatment. Fact tables may be maintained for each of the patients involved for time of study, time since initial treatment, cumulative dosage, patient's weight, size, gender, age, race and the like. The database 217 may be configured to normalize the information collected about each of the patients so that a first dose reaction of a first patient may be compared to a first dose reaction of a second patient even though the first patient began the program 4 years before the second patient. Furthermore, the database 217 may be further configured to select participants having a similar size (height, weight, frame), gender, age and the like to further remove any outside factors that may effect the way a dose of the drug may effect the participant. These groups sharing similar qualities may be termed cohorts.

It will be understood that databases that are not written in a format according to embodiments of the present invention may interact with the database 217 according to some embodiments of the present invention. For example, if an entity stores patient information in an Excel spreadsheet, the Excel spreadsheet is not in the fact table/dimension table format as discussed herein. However, an identification key may be established for the Excel spreadsheet and/or the information stored therein and these identification keys may be included in fact tables according to some embodiments of the present invention. Thus, information provided in the Excel spreadsheet may be accessed through queries of the database 217.

It will be understood that teachings of the present invention may be combined with any relational database management system, such as DB2 and Oracle. It will be further understood that the database 217 according to some embodiments of the present invention is customizable by the customer.

Figure 4:
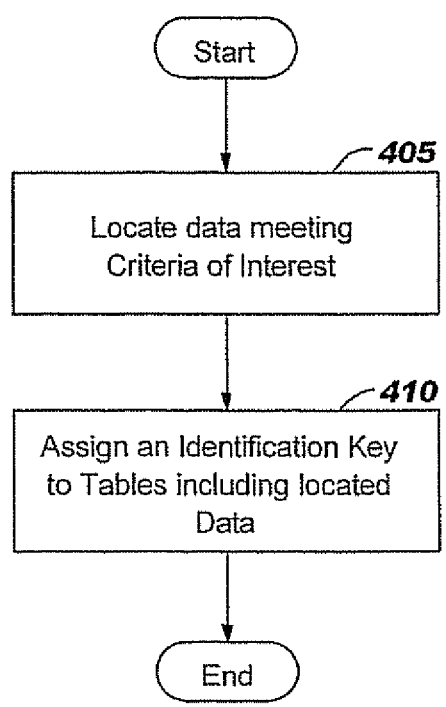
FIG. 4 is flowchart illustrating operations according to some embodiments of the present invention.

Operations according to some embodiments of the present invention will now be discussed with respect to FIGS. 4 and 5. Referring now to FIG. 4, operations begin at block 405 by locating data meeting a criteria of interest in at least two fact tables stored in a healthcare database. The criteria of interest may be, for example, a medical condition, such as diabetes or heart disease, a participant in a particular medical study, a reaction to a particular drug or family of drugs or the like. An identification key may be assigned to the fact tables including the located data meeting the criteria of interest so as to allow future identification of the fact tables using the identification key (block 410). In other words, the fact tables including the criteria of interest are provided with an additional identification key to store therein. The identification key points to a dimension table indicating the identification keys of subjects associated with the fact tables that met the criteria of interest. The dimension tables may enable additional facts and supporting dimensional information to be found. This may allow researchers to iterate through the data looking for additional interesting and relevant information. Furthermore, when accessing this information in the future, the entire database does not have to be searched.

Referring now to FIG. 5, operations begin at block 500 by generating a database having fact tables and dimension tables according to some embodiments of the present invention. As discussed above, the generated database may be customized by the user of user(s). The generated database may be physically instantiated, federated or a combination of both. A first criteria of interest may be located in at least two fact tables stored in a healthcare database (block 505). A first identification key may be assigned to the fact tables including the located data meeting the criteria of interest so as to allow future identification of the fact tables using the identification key (block 510). A second criteria of interest may be located in at least two fact tables stored in the healthcare database (block 520) and a second identification key may be assigned to the fact tables including the located data meeting the second criteria of interest (block 525). A third identification key may be assigned to ones of the fact tables having both the first and second assigned identification keys (block 530). Thus, a compound index or dimension table may be created including identification keys associated with patients having both diabetes and heart disease. In some embodiments of the present invention the third identification key may be automatically assigned.

It will be understood that in some embodiments of the present invention, the information found in the fact tables may not be revealed to the researcher unless the researcher is authorized to view the information in the fact tables. The issue of authorization typically occurs when multiple groups of entities share a single database environment, but do not wish to share all the information stored therein as discussed above.

In some embodiments of the present invention, the generated database (500) is generated for a medical study. Individuals may enter the study at various times and, therefore, may all be at different stages of their treatment. The generated database may be configured to normalize the information collected about each of the patients so that a first dose reaction of a first patient may be compared to a first dose reaction of a second patient even though the first patient began the program 4 years before the second patient (block 535). As discussed above, the normalized data may be further broken down into participants having a similar size (height, weight, frame), gender, age and the like to further remove any outside factors that may effect the way a dose of the drug may effect the participant.

Databases according to some embodiments of the present invention, allow a researcher to have multiple frames of reference. Once the data intersections have been made the data may then be viewed from many different perspectives, for example, patient, associated patient facts, fact values, such as lab tests results and the like, to provide answers. Furthermore, databases according to some embodiments of the present invention may be used to look for combinations of combinations. In other words, databases according to some embodiments of the present invention may be configured to look for similarities and differences between entities of interest, mark down those similarities or differences and find combinations of the similarities or differences. Then, the results may be used to research and analyze the data from many perspectives using manual observation, simple query tools, simple statistical tools or very complex statistical tools.

Many alterations and modifications may be made by those having ordinary skill in the art, given the benefit of present disclosure, without depa9407-rting from the spirit and scope of the invention. Therefore, it must be understood that the illustrated embodiments have been set forth only for the purposes of example, and that it should not be taken as limiting the invention as defined by the following claims. The following claims are, therefore, to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

That which is claimed is:

1. A system for relating facts stored in healthcare databases, the system comprising:
a location circuit, implemented in a processor, configured to locate data meeting a criteria of interest in at least two fact tables stored in a healthcare database; and
an identification circuit, implemented in the processor, configured to assign a single identification key to the at least two fact tables including the located data meeting the criteria of interest, the identification key providing access to a dimension table including a list of subjects associated with the at least two fact tables including the located data meeting the criteria of interest, wherein the identification key premarks the subjects associated with the at least two fact tables including the criteria of interest to facilitate future access to the subjects satisfying the criteria of interest without having to search all of the healthcare database again for the criteria of interest.

2. The system of claim 1:
wherein the criteria of interest comprises a first criteria of interest;
wherein the identification key comprises a first identification key;
wherein the dimension table comprises a first dimension table;
wherein the location circuit is further configured to locate data meeting a second criteria of interest in at least two fact tables stored in the healthcare database; and
wherein the identification circuit is further configured to:
assign a second identification key to the at least two fact tables including the located data meeting the second criteria of interest, the second identification key providing access to a second dimension table including a list of subjects associated with the at least two fact tables including the second criteria of interest so as to allow future identification of the subjects meeting the second criteria of interest; and
assign a third identification key to subjects meeting the first and second criteria of interest, the third identification key providing access to a third dimension table including a list of subjects meeting both the first and second criteria of interest so as to allow future identification of the subjects meeting the first and second criteria of interest.

3. The system of claim 2, wherein the identification circuit is further configured to automatically assign the third identification key.

4. The system of claim 1, wherein the located data is associated with a medical study, the system further comprising a normalization circuit configured to normalize the data associated with the medical study so as to allow direct comparison of the data.

5. The system of claim 1, further comprising a database circuit configured to generate a database environment including a plurality of fact tables and a plurality of associated dimension tables.

6. The system of claim 5, wherein the plurality of fact tables are divided into a plurality of groups of fact tables and wherein each of the plurality of groups are associated with an entity, the system further comprising:
an authorization circuit configured to provide authorization codes to each entity, the authorization codes providing access to at least one of the groups of fact tables.

7. The system of claim 6, wherein the plurality of fact tables include at least one identification key which identifies an associated dimension table, wherein the associated dimension table includes information that further describe facts provided in the plurality of fact tables and wherein the plurality of fact tables are related through the plurality of dimension tables.

8. A computer program product for relating facts stored in healthcare databases, the computer program product comprising:
a non-transitory computer readable storage medium having computer readable program code embodied in said medium, the computer readable program code comprising:
computer readable program code configured to locate data meeting a criteria of interest in at least two fact tables stored in a healthcare database; and
computer readable program code configured to assign a single identification key to the at least two fact tables including the located data meeting the criteria of interest, the identification key providing access to a dimension table including a list of subjects associated with the at least two fact tables including the located data meeting the criteria of interest, wherein the identification key premarks the subjects associated with the at least two fact tables including the criteria of interest to facilitate future access to the subjects satisfying the criteria of interest without having to search all of the healthcare database again for the criteria of interest.

9. The computer program product of claim 8, wherein the criteria of interest comprises a first criteria of interest and wherein the identification key comprises a first identification key, the computer program product further comprising:
computer readable program code configured to locate data meeting a second criteria of interest in at least two fact tables stored in the healthcare database;
computer readable program code configured to assign a second identification key to the at least two fact tables including the located data meeting the second criteria of interest, the second identification key providing access to a second dimension table including a list of subjects associated with the at least two fact tables including the second criteria of interest so as to allow future identification of the subjects meeting the second criteria of interest; and
computer readable program code configured to assign a third identification key to subjects meeting the first and second criteria of interest, the third identification key providing access to a third dimension table including a list of subjects meeting both the first and second criteria of interest so as to allow future identification of the subjects meeting the first and second criteria of interest.

10. The computer program product of claim 9, wherein the computer readable program code configured to assign a third identification key comprises computer readable program code configured to automatically assign the third identification key.

11. The computer program product of claim 8, wherein the located data is associated with a medical study, the computer program product further comprising computer readable program code configured to normalize the data associated with the medical study so as to allow direct comparison of the data.

12. The computer program product of claim 8, further comprising:
computer readable program code configured to generate a database environment including a plurality of fact tables and a plurality of associated dimension tables, the plurality of fact tables being divided into a plurality of groups of fact tables and each of the plurality of groups being associated with an entity; and
computer readable program code configured to provide authorization codes to each entity, the authorization codes providing access to at least one of the groups of fact tables.

13. The computer program product of claim 12, wherein the plurality of fact tables include at least one identification key which identifies an associated dimension table, wherein the associated dimension table includes information that further describe facts provided in the plurality of fact tables and wherein the plurality of fact tables are related through the plurality of dimension tables.

* * * * *